United States Patent [19]

Beavers et al.

[11] Patent Number: 5,770,575
[45] Date of Patent: Jun. 23, 1998

[54] NIPECOTIC ACID DERIVATIVES AS ANTITHROMBOTIC COMPOUNDS

[75] Inventors: Mary Pat Beavers, Warrington; Patricia Andrade-Gordon, Doyletown; William J. Hoekstra, Bryn Mawr, all of Pa.

[73] Assignee: Ortho Pharmaceutical Corporation, Raritan, N.J.

[21] Appl. No.: 395,533

[22] Filed: Mar. 6, 1995

Related U.S. Application Data

[63] Continuation-in-part of Ser. No. 364,896, Dec. 27, 1994, abandoned, which is a continuation-in-part of Ser. No. 213,772, Mar. 16, 1994, abandoned.

[51] Int. Cl.⁶ .................................................. A61K 38/00
[52] U.S. Cl. .............................. 514/19; 514/18; 530/331; 546/187; 546/208; 546/247
[58] Field of Search ....................... 514/18–19; 546/187, 546/208, 247; 530/331

[56] References Cited

U.S. PATENT DOCUMENTS

| | | | |
|---|---|---|---|
| 4,857,508 | 8/1989 | Adams et al. | 514/18 |
| 5,318,899 | 6/1994 | Scarborough et al. | 435/69.6 |
| 5,352,667 | 10/1994 | Lider et al. | 514/19 |
| 5,358,934 | 10/1994 | Borovsky et al. | 514/17 |
| 5,559,209 | 9/1996 | Nishimoto | 530/326 |

OTHER PUBLICATIONS

Fauchere et al., Int. J. Peptide Prot. Res. vol. 42 Nov. 1993 pp. 440–444.

*Primary Examiner*—Cecilia J. Tsang
*Assistant Examiner*—Bennett Celsa
*Attorney, Agent, or Firm*—Ralph R. Palo

[57] ABSTRACT

Nipecotic acid-derived compounds of formula (I):

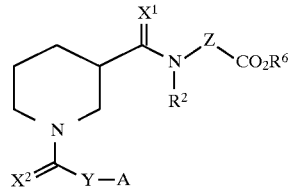

are disclosed as useful in treating platelet-mediated thrombotic disorders.

7 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

His His Leu Gly Gly Ala Lys Gln Ala Gly Asp Val
    1                    5                              10

NIPECOTIC ACID DERIVATIVES AS ANTITHROMBOTIC COMPOUNDS

This is a continuation-in-part of application Ser. No. 08/364,896, filed Dec. 27, 1994 (Abn), which application is a continuation-in-part of application Ser. No. 08/213,772, filed Mar. 16, 1994 (Abn).

BACKGROUND OF THE INVENTION

Platelet aggregation constitutes the initial hemostatic response to curtail bleeding induced by vascular injury. However, pathological extension of this normal hemostatic process can lead to thrombus formation. The final, common pathway in platelet aggregation is the binding of fibrinogen to activated, exposed platelet GPIIb/IIIa. Agents which interrupt binding of fibrinogen to platelet glycoprotein IIb/IIIa (GPIIb/IIIa), therefore, inhibit platelet aggregation. These agents are, therefore, useful in treating platelet-mediated thrombotic disorders such as arterial and venous thrombosis, acute myocardial infarction, unstable angina, reocclusion following thrombolytic therapy and angioplasty, inflammation, and a variety of vaso-occlusive disorders. The fibrinogen receptor (GPIIb/IIIa) is activated by stimuli such as ADP, collagen, and thrombin exposing binding domains to two different peptide regions of fibrinogen: α-chain Arg-Gly-Asp (RGD) and γ-chain His-His-Leu-Gly-Gly-Ala-Lys-Gln-Ala-Gly-Asp-Val [SEQ. ID. NO.: 1] (HHLGGAKQAGDV, γ400–411). Since these peptide fragments themselves have been shown to antagonize (inhibit) fibrinogen binding to GPIIb/IIIa, a mimetic of these fragments would also serve as an antagonist. In fact, prior to this invention, potent RGD-based or RGD mimetic antagonists have been revealed which inhibit both fibrinogen binding to GPIIb/IIIa and platelet aggregation. Some of these agents have also shown in vivo efficacy as antithrombotic agents and, in some cases, have been used in conjunction with fibrinolytic therapy (e.g., t-PA or streptokinase) as well.

DISCLOSURE OF THE INVENTION

The present invention is directed to compounds represented by the following general formula (I):

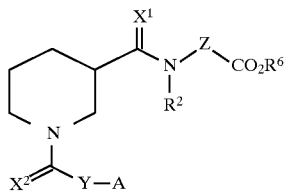

wherein $X^1$, $X^2$, Y, Z, $R^2$ and A are as hereinafter defined. Such compounds, based upon structural features of fibrinogen γ400–411, are platelet aggregation inhibitors useful in treating platelet-mediated thrombotic disorders such as arterial and venous thrombosis, acute myocardial infarction, reocclusion following thrombolytic therapy and angioplasty, inflammation and unstable angina and a variety of vaso-occlusive disorders. These compounds are also useful as antithrombotics used in conjunction with fibrinolytic therapy (e.g., t-PA or streptokinase). Pharmaceutical compositions containing such compounds are also part of the present invention.

DETAILED DESCRIPTION OF THE INVENTION

More particularly, the present invention is directed to compounds of the following formula (I):

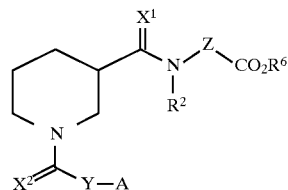

wherein $X^1$ and $X^2$ are the same or different and selected from either of $H_2$ or O. Preferably, each of $X^1$ and $X^2$ is O.

Y is $(CH_2)m$, $CH(NHCOR^3)(CH_2)m$, or $CH(NH_2)CH_2)m$.

A is $NHR^1$, $C(NH)NH_2$ or a cycloalkyl ring containing a nitrogen therein which ring is selected from any of piperidin-2-yl, piperidin-3-yl, piperidin-4-yl, pyrrolidin-2-yl and pyrrolidin-3-yl. More preferably, the ring is selected from any of piperidin-2-yl, piperidin-3-yl, or piperidin-4-yl.

Z is $(CH_2)n$ or $CH(CO_2R^4)(CH_2)n$. Preferably, Z is $(CH_2)_2$.

$R^1$ is H, alkyl, or $CH(NH)NH_2$. More preferably, $R^1$ is H or alkyl. Most preferably, $R^1$ is hydrogen $R^2$ is H or alkyl. Preferably, $R^2$ is hydrogen.

$R^3$ is alkoxy or alkyl. Preferably, $R^3$ is t-butoxy or methyl. Most preferably, $R^3$ is t-butoxy.

$R^4$ is alkyl or arylalkyl such as benzyl. Preferably, $R^4$ is methyl.

$R^6$ is H, alkyl or arylalkyl such as benzyl. When $R^6$ is other than H, it is in its prodrug form.

m is the integer 0, 1, 2, or 3.

n is the integer 0, 1, or 2.

As used herein, unless otherwise noted alkyl and alkoxy whether used alone or as part of a substituent group, include straight and branched chains having 1–8 carbons. For example, alkyl radicals include methyl, ethyl, propyl, isopropyl, n-butyl, isobutyl, sec-butyl, t-butyl, n-pentyl, 3-(2-methyl)butyl, 2- pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 5–8 ring carbons and preferably 6–7 carbons.

The term "aryl" as used herein alone or in combination with other terms indicates aromatic hydrocarbon groups such as phenyl or naphthyl. The term "arylalkyl" means an alkyl group substituted with an aryl group.

The compounds of the present invention may also be present in the form of a pharmaceutically acceptable salt. The pharmaceutically acceptable salt generally takes a form in which the nitrogen on the 1-piperidine substituent is protonated with an inorganic or organic acid. However when $X^2$ is $H_2$ the ring nitrogen may be subject to salt formation. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharic or trifluoroacetic.

Particularly preferred compounds of the present invention include compounds represented by the formula:

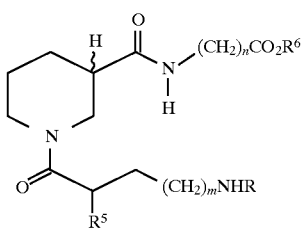

| | |
|---|---|
| R=H m=3 n=2 R⁵=L-NHBoc R⁶ is benzyl (Bn) | (CP #1); |
| R=H m=3 n=2 R⁵=L-NHBoc R⁶ is H | (CP #2); |
| R=H m=3 n=2 R⁵=D-NHBoc R⁶ is H | (CP #3); |
| R=H m=3 n=2 R⁵=L-NH₂ R⁶ is H | (CP #4); |
| R=H m=3 n=2 R⁵=-H R⁶ is H | (CP #5); |
| R=H m=3 n=1 R⁵=L-NHAcR⁶ is H | (CP #6); |
| R=H m=3 n=2 R⁵=L-NHAc R⁶ is H | (CP #7); |
| R=C(NH)NH₂ m=2 n=2 R⁵-L-NHBoc R⁶ is H | (CP #8); |
| R=H m=3 n=3 R⁵=L-NHBoc R⁶ is H | (CP #9); |
| R=H m=3 n=2 R⁵=D-NH₂ R⁶ is H | (CP #10); |
| R=H m=3 n=3 R⁵=D-NHBoc R⁶ is H | (CP #11); |
| R=H m=3 n=1 R⁵=D-NHBoc R⁶ is H | (CP #12); |
| R=H m=3 n=2 R⁵=D-NHAc R⁶ is H | (CP #13); |
| 3-S-isomer of CP#3 R⁶ is H | (CP #14); |
| R=i-Pr m=3 n=2 X=L-NHBoc R⁶ is H | (CP #15); |
| 3-R-isomer of CP#3 R⁶ is H | (CP #16); |

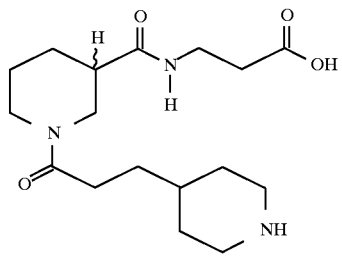

CP #17

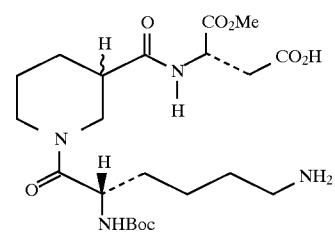

CP #18

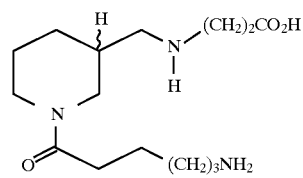

CP #19

The compounds of the invention may be prepared from commercially available starting materials by the following reaction schemes M, AB, AC and AD.

The compounds of the invention where $X^1$ and $X^2$ are each oxygen may be prepared by following scheme AA. In this scheme nipecotic acid (either the racemic mixture or either separate enantiomer) may be treated with a lower alkyl alcohol and a catalytic amount of an acid from about room temperature to reflux, to give the ester derivative AA1 as the acidic salt. Typical alcohols which include ethanol, methanol, isopropanol and butanol may be paired with acidic catalysts such as p-toluenesulfonic acid, HCI or sulfuric acid. The preferred reagents are methanol and HCI. Derivative AA1 may be acylated at the ring nitrogen with a variety of acylating agents to give derivative AA2. Typical reaction conditions include treating AA1 with the acylating agent and an equivalent of an organic base in an inert solvent at room temperature for 15 min to 2 h. The preferred acylating agents are amino protected amino acids or amino protected aminoalkyl carboxylic acids, which are activated with coupling reagents such as DCC (1,3-dicyclohexylcarbodii mide) and BOP-CI (bis(2-oxo-3-oxazolidi nyl)phosphinic chloride). However, amino protected acid derivatives such as anhydrides, N-oxysuccinimides, and acid chlorides may also be used. Suitable protecting groups include lower alkyl carbamates, branched alkyl carbamates, benzyl carbamates, acetamides, and substituted acetamides. The choice of acylating agent and its amino protecting group(s) is the factor that determines substituents Y and $R^1$ in the compounds of Formula I where $X^1$ and $X^2$ are O. In Scheme AA, the protected amino acid is the diamino acid of the formula NH(Boc)CHCO₂H(CH₂)ₙN(Cbz), which allows for selective deprotection of the two amino groups at a latter point in the scheme. This choice is only meant to illustrate the invention and not to limit it.

Derivative AA2 can be treated with a base and a suitable solvent mixture to give the salt derivative AA3. Suitable inorganic bases include NaOH, KOH, Mg(OH)₂, LiOH, Na₂CO₃ and NaHCO₃, which may be combined with mixtures of THF and water at room temperature for 1–6 h to give the desired product. The organic bases which may be used include triethylamine, tributylamine, diisopropylethylamine and tetramethylguanidine. These bases can be used with organic solvents at room temperature to reflux for 1–6 h to give salt AA3.

The preferred reaction conditions (which are illustrated) are the treatment of AA2 with LiOH, water and THF at room temperature for 1 h. Other suitable inorganic basis may be used such as NaOH, KOH, Mg(OH)₂, NaCO₃ and NaHCO₃. Should another such base be used, the Li in AA3 would, of course, be replaced by the appropriate metal substituent. Derivative AA3 may be treated with a carboxy protected carboxyalkylamine or a carboxy protected amino acid under standard amino acid coupling conditions to give the disubstituted nipecotic derivative AA4. Acceptable coupling conditions include employing peptide coupling agents such as DCC, BOP-CI and EDC (ethyl dimethylaminopropylcarbodiimide.HCl). Suitable carboxy protecting groups include benzyl carbamates, substituted benzyl carbamates, alkyl carbamates and branched alkyl carbamates where the choice of protecting group is obvious to those skilled in chemical synthesis. The illustrated example uses NH₂(CH₂)nCO₂-(Bzl) as the protected amino acid. Once again the choice of amino acid and its carboxy protecting group determine substituents $R^2$ and Z in the compounds of Formula I where $X^1$ and $X^2$ are O. Derivative AA4 may be selectively deprotected in accordance with the the requirements of the amino or carboxy protecting group. In the illustrated example, the protecting groups on the 3-carboxy group and one of the amino groups are simultaneously removed by catalytic hydrogenation using Pd/C in a $H_2$ atmosphere to give derivative AA5.

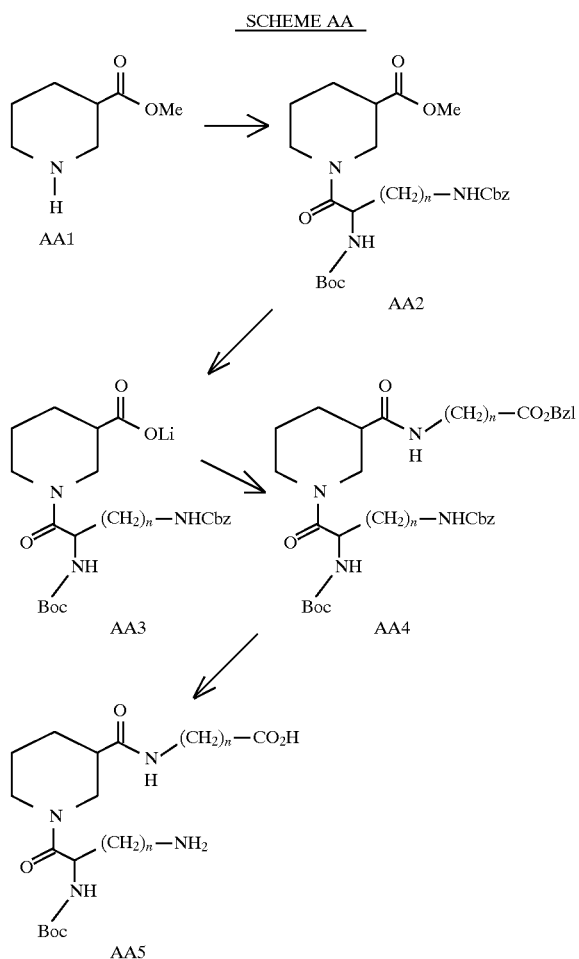

Scheme AB illustrates the preparation of compounds of Formula I where $X^2$ is O and $X^1$ is $H_2$ Nipecotic acid (either the racemic mixture or either separate enantiomer) may be treated with a alkyl alcohol and a catalytic amount of an acid from about room temperature to reflux, to give the ester derivative AB1 as the acidic salt. Typical alcohols include ethanol, methanol, isopropanol and butanol. The acid catalysts include p-toluenesulfonic acid, HCI and sulfuric acid where the preferred reagents are methanol and HCI. Derivative AB1 may be acylated at the ring nitrogen with a variety of acylating agents to give derivative AB2. Typical reaction conditions include treating AB1 with the acylating agent and an equivalent of an organic base in an inert solvent at room temperature for 15 min to 2 h. The preferred acylating agents are amino protected amino acids or amino protected aminoalkyl carboxylic acids, which are activated with coupling reagents such as DCC (1,3-dicyclohexylcarbodiimide) and BOP-CI (bis(2-oxo-3-oxazolidinyl)phosphinic chloride). However, amino protected acid derivatives such as anhydrides, N-oxysuccinimides and acid chlorides may also be used. Suitable protecting groups include lower alkyl carbamates, branched alkyl carbamates, benzyl carbamates, acetamides, and substituted acetamides. The choice of amino acid and its amino protecting group(s) is the factor that determines substituents Y and $R^1$ in the compounds of Formula I. In Scheme AB, the protected amino acid is the diamino acid of the formula $NH(Boc)CHCO_2H(CH_2)_nN$ (Boc), this choice is only meant to illustrate the invention and not to limit it. Derivative AB2 can be hydrolyzed with a base and a suitable solvent mixture to give derivative AB3. Suitable inorganic bases include NaOH, KOH, $Mg(OH)_2$, LiOH, $Na_2CO_3$ and $NaHCO_3$, which may be combined with mixtures of THF and water at room temperature for 1-6 h to give the desired product. The organic bases which may be used include triethylamine, tributylamine, diisopropylethylamine and tetramethylguanidine. These bases can be used with organic solvents at room temperature to reflux for 1–6 h to give AB3. The 3-carboxy group of derivative AB3 may be reduced to give the aldehyde derivative AB4 by using a number of reaction condidtions. Those conditions include the use of lithium t-diisopropylamide with HMPT/THF as a solvent from $-78°$ to $0°$ C., N,N-dimethylchloromethyleniminium chloride and lithium t-butoxyaluminum hydride with pyridine as a solvent at $-78°$ C. and standard Rosenmund reduction conditions. The preferred reaction conditions use N,N'-carbonyidiimidazole followed by diisobutylaluminum hydride at $-10°$ C. to give the aldehyde derivative AB4. AB4 may be treated with a carboxy protected carboxyalkylamine or a carboxy protected amino acid followed by a reducing agent to give the disubstituted nipecotic derivative AB5. Suitable carboxy protecting groups include benzyl carbamates, substituted benzyl carbamates, lower alkyl carbamates and branched alkyl carbamates where the choice of protecting group is obvious to those skilled in chemical synthesis. Reducing agents include sodium cyanoborohydride, lithium cyanoborohydride, sodium-9-cyano-9-hydrido-borabicyclo [3,3, 1] nonane, tetrabutylammoniu m cyanoborohydride and Pd/C with an acidic solvent where the choice of reducing agent is determined by the protecting groups in use. The illustrated example uses $NH_2(CH_2)_nCO_2Bzl$ as the protected amino acid and sodium cyanoborohydride as a reducing agent. This choice of amino acid and its carboxy protecting group determine substituents $R^2$ and Z in the compound and is meant to be illustrative not limiting. Derivative AB5 may be selectively deprotected in accordance with the the requirements of the amino or carboxy protecting group. As illustrated example, the protecting groups on the 3-carboxy group and both amino groups are simultaneously removed by catalytic hydrogenation using Pd/C in a $H_2$ atmosphere to give derivative AB6.

SCHEME AB

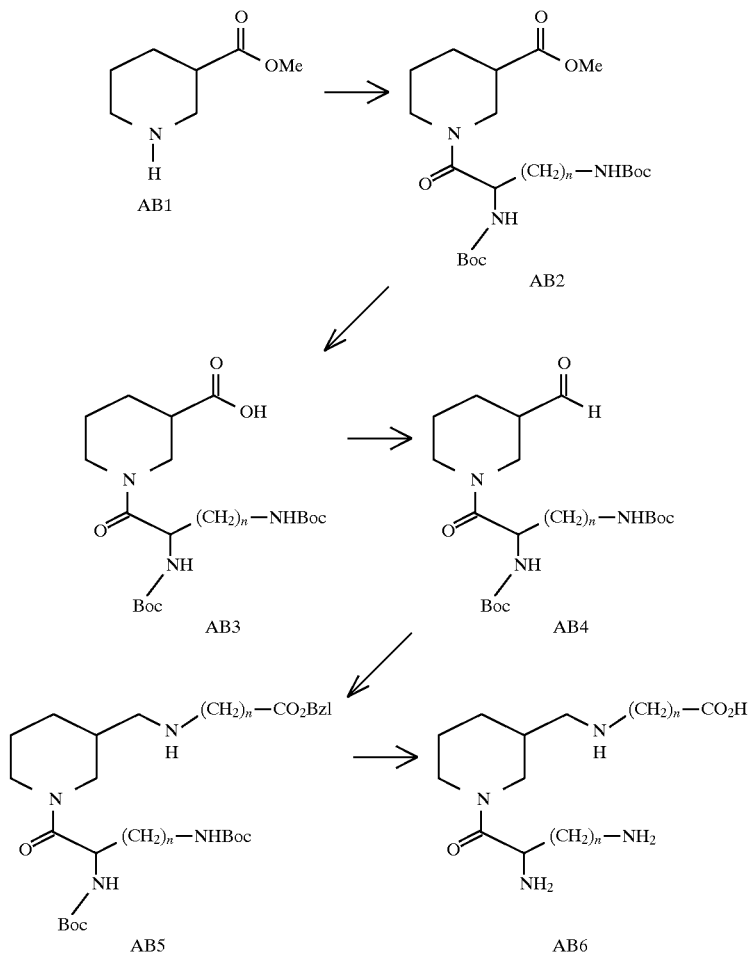

The compounds of the invention where $X^1$ is oxygen and $X^2$ is $H_2$ and may be prepared by following scheme AC. In this scheme nipecotic acid (either the racemic mixture or the separated enantiomers) may be treated with a lower alkyl alcohol and a catalytic amount of an acid from about room temperature to reflux, to give the ester derivative AC1 as the acidic salt. Typical alcohols include ethanol, methanol isopropanol and butanol. The acid catalysts include p-toluenesulfonic acid, HCl and sulfuric acid.with methanol and HCl as the reagents of choice. Derivative AC1 may be alkylated at the ring nitrogen with an alkylating agent to give derivative AC2. Alkylating reagents include haloalkylamine synthons such as bromoalkylphthalimides and bromoalkylnitriles, or protected aminoaldehydes via reductive amination procedures ( for conditions, see Scheme AD). Typical reaction conditions include treating AC1 with a base such as sodium hydride or a phase transfer catalyst such as tetrabutylammonium fluoride and an alkylating agent in an inert solvent at room temperature for 15 min to 2 h followed by routine protection of the 3-substituent's amino group with any of the aforementioned suitable protecting groups. The choice of alkylating agent and its amino protecting group is the factor that determines substituents Y and $R^1$. In Scheme AC the 1- position is substituted with $(CH_2)NH$ (Cbz), a choice that is only meant to illustrate the invention and not to limit it. Derivative AC2 can be treated with a base and a suitable solvent mixture to give the salt derivative AC3. As in Scheme AA, Scheme AC shows the use of the preferred LiOH. However, other suitable inorganic bases include NaOH, KOH, $Mg(OH)_2$, $Na_2CO_3$ and $NaHCO_3$, which may be combined with mixtures of THF and water at room temperature for 1–6 h to give the desired product. The organic bases which may be used include triethylamine, tributylamine, diisopropylethylamine and tetramethylguanidine. These bases can be used with organic solvents at room temperature to reflux for 1–6 h to give salt AC3. The preferred reaction conditions (which are illustrated) are the treatment of AC2 with LiOH, water and THF at room temperature for 1 h. Derivative AC3 may be treated with a carboxy protected carboxyalkylamine or a carboxy protected amino acid under standard amino acid coupling conditions to give the disubstituted nipecotic derivative AC4. Acceptable coupling conditions include employing peptide coupling agents such as DCC, BOP-Cl and EDC (ethyl dimethylaminopropyl carbodiimide•HCl). Suitable carboxy protecting groups include benzyl carbamates, substituted benzyl carbamates, alkyl carbamates and branched alkyl carbamates where the choice of protecting group is obvious to those skilled in chemical synthesis. The illustrated example uses $NH_2(CH_2)_nCO_2Bzl$ as the protected amino acid. Once again the choice of amino acid and its carboxy protecting group determine substituents $R^2$ and Z in the compounds of Formula I. Derivative AC4 may be selectively deprotected in accordance with the the requirements of the amino or carboxy protecting group. In the illustrated example, the protecting groups on the 3-carboxy group and the 1-amino group are simultaneously removed by catalytic hydrogenation using Pd/C in a H$_2$ atmosphere to give derivative AC5.

SCHEME AC

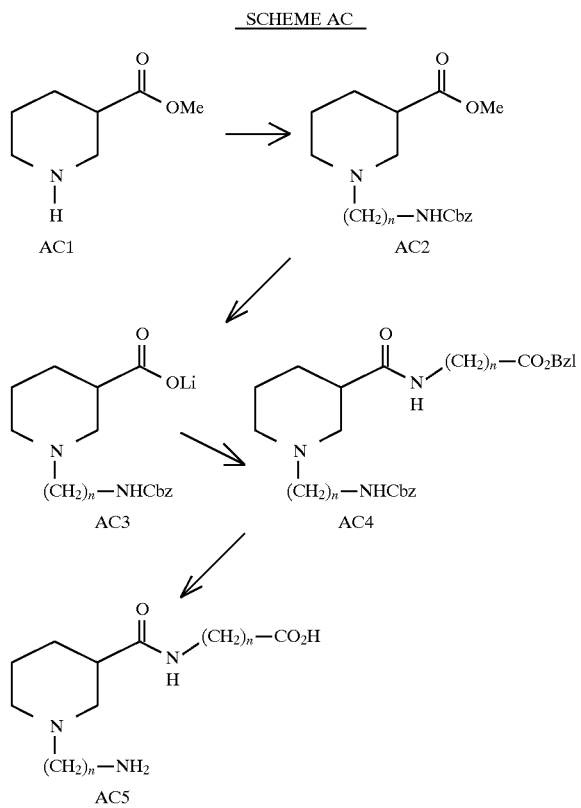

The compounds of the invention where X$^1$ and X$^2$ are each H$_2$ and may be prepared by following scheme AD. In this scheme nipecotic acid (either the racemic mixture or the separated enantiomers) may be treated with a lower alkyl alcohol and a catalytic amount of an acid from about room temperature to reflux, to give the ester derivative AD1 as the acidic salt. Typical alcohols include ethanol, methanol isopropanol and butanol. The acid catalysts include p-toluenesulfonic acid, HCl and sulfuric acid. The preferred reagents are methanol and HCl. Derivative AD1 may be alkylated at the ring nitrogen with an alkylating agent to give derivative AD2. Alkylating reagents include haloalkylamine synthons such as bromoalkylphthalimides and bromoalkylnitriles, or protected aminoaldehydes via reductive amination procedures (for conditions, see Scheme AD).

Typical reaction conditions include treating AD1 with a base such as sodium hydride or a phase transfer catalyst such as tetrabutylammonium fluoride and an alkylating agent in an inert solvent at room temperature for 15 min to 2 h followed by routine protection of the amino group with any of the aforementioned suitable protecting groups. The choice of alkylating agent and its amino protecting group is the factor that determines substituents Y and R$^1$. In Scheme AD the 1-position is substituted with (CH$_2$)NH(Cbz), a choice that is only meant to illustrate the invention. Derivative AD2 can be hydrolyzed with a base and a suitable solvent mixture to give derivative AD3. Suitable inorganic bases include NaOH, KOH, MgOH, LiOH, Na$_2$CO$_3$ and NaHCO$_3$, which may be combined with mixtures of THF and water at room temperature for 1–6 h to give the desired product. The organic bases which may be used include triethylamine, tributylamine, diisopropylethylamine and tetramethylguanidine. These bases can be used with organic solvents at room temperature to reflux for 1–6 h to give AD3. The 3-carboxy group of derivative AD3 may be reduced to give the aldehyde derivative AD4 by using a number of reaction condidtions. Conditions include the use of lithium diisopropylamide with HMPT/THF as a solvent from –78° to 0° C., N,N-dimethylchloromethyleniminium chloride and lithium 1-butoxyaluminum hydride with pyridine as a solvent at –78° C. and standard Rosenmund reduction conditions. The preferred reaction conditions use N,N'-carbonyldiimidazole followed by diisobutylaluminum hydride at –10° C. to give the aldehyde derivative AD4.

Derivative AD4 may be treated with a carboxy protected carboxyalkylamine or a carboxy protected amino acid followed by a reducing agent to give the disubstituted nipecotic derivative AD5. Suitable carboxy protecting groups include benzyl carbamates, substituted benzyl carbamates, lower alkyl carbamates and branched alkyl carbamates where the choice of protecting group is obvious to those skilled in chemical synthesis. Reducing agents include sodium cyanoborohydride, lithium cyanoborohydride, sodium-9-cyano-9-hydrido-borabicyclo[3,3, 1] nonane, tetrabutylammonium cyanoborohydride and Pd/C with an acidic solvent where the choice of reducing agent is determined by the protecting groups in use. The illustrated example uses NH$_2$(CH$_2$)$_n$CO$_2$Bzl as the protected amino acid and sodium cyanoborohydride as a reducing agent. This choice of amino acid and its carboxy protecting group determine substituents R$^2$ and Z in the compound and is meant to be illustrative not limiting. Derivative AD5 may be selectively deprotected in accordance with the requirements of the amino or carboxy protecting group. As illustrated, the protecting groups on the 3-carboxy group and the amino group are simultaneously removed by catalytic hydrogenation using Pd/C in a H$_2$ atmosphere to give derivative AD6.

SCHEME AD

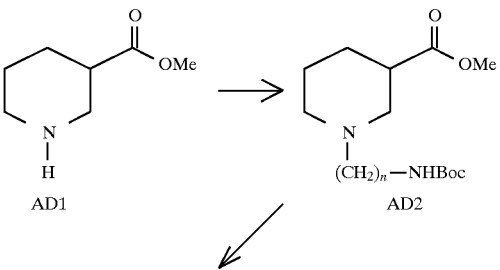

-continued
SCHEME AD

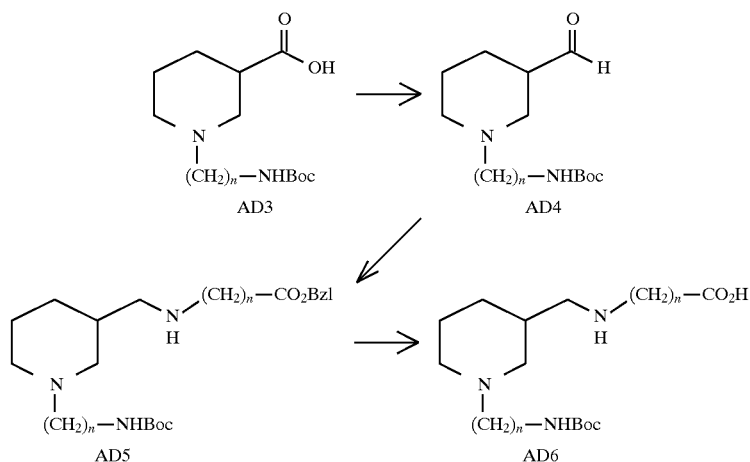

With regard to starting materials for all schemes, most of the amino acids and the aminoalkylcarboxylic acids needed to produce compounds where A is $NHR^1$, are commercially available and only require the manipulation of protecting groups to give the desired compounds of Formula I. However, to produce the compounds of the invention where A is a cycloalkyl ring containing a nitrogen therein, the 1-substituent (piperidine) must be modified after addition to give desired compounds of Formula I. To produce the compounds where the 1-substituent is $C(O)(CH_2)_2$-4-yl-piperdine, derivatives AA1 or AB1 are acylated with 3-(4-pyridyl)acrylic acid to produce the acylated derivatives AA2 and AB2, using the aforementioned acylation procedures. These derivatives are converted as described in the schemes to give AA4 and AB5. Derivatives AA5 and AB6 may be produced by treating AA4 and AA5 with a suitable reducing agent which in this case removes the protecting group on the carboxy group of the 3-position and reduces the ethylene-substituted pyridine to give the desired compound. The preferred reducing/deprotecting agent is $PtO_2$. The 2 and 3-yl piperidines may be produced by modifying the acrylic acid derivative by conventional means.

To produce the compounds where the 1-substituent is $C(O)(CH_2)_2$-3-yl-pyrrole, derivatives AA1 or AB1 are acylated with 3-(1-benzylpyrrolidin-3-yl)acrylic acid to produce the acylated derivatives AA2 and AB2, using the aforementioned acylation procedures. This substituted pyrrole acrylic acid derivative may be obtained by hydrolyzing the corresponding nitrile derivative with aqueous acid. 3-(1-Benzylpyrrolidin-3-yl)acrylonitrile was synthesized according to the methods described in U.S. Pat. No. 4,002,643, which is incorporated herein by reference. These derivatives are treated as described above (for the six-membered case) to give the compounds of the invention where A is a five-membered ring with a nitrogen contained therein.

To produce diastereomerically-enriched final compounds which contain the Boc-D-Lys and either R- or S-nipecotyl groups (see compounds 14 and 16), the corresponding enantiomerically-enriched nipecotic acid methyl esters were employed at the beginning of the syntheses. Enantiomerically-enriched nipecotic acid methyl esters were isolated by chiral resolution of racemic material as published (A. M. Akkerman, Rec. Trav. Chim. Pays-Bas 1951, 70, 899).

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intra muscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

PHARMACOLOGY

The compounds of the present invention interrupt binding of fibrinogen to platelet glycoprotein IIb/IIIa (GPIIb/IIIa)

and thereby inhibit platelet aggregation. Such compounds are, therefore, useful in treating platelet-mediated thrombotic disorders such as arterial and venous thrombosis, acute myocardial infarction, reocclusion following thrombolytic therapy and angioplasty, and a variety of vaso-occlusive disorders. Because the final, common pathway in normal platelet aggregation is the binding of fibrinogen to activated, exposed GPIIb/IIIa, inhibition of this binding represents a plausible antithrombotic approach. The receptor is activated by stimuli such as ADP, collagen, and thrombin, exposing binding domains to two different peptide regions of fibrinogen: α-chain Arg-Gly-Asp (RGD) and γ-chain 400–411. As demostrated by the results of the pharmacological studies described hereinafter, the compounds of the present invention have shown the ability to block fibrinogen binding to isolated GPIIb/IIa ($IC_{50}$'s 3–5800 nM), inhibit platelet aggregation in vitro in the presence of a various of platelet stimuli, and furthermore, have inhibited ex vivo platelet aggregation in animal models.

IN VITRO SOLID PHASE PURIFIED GLYCOPROTEIN IIB/IIIA BINDING ASSAY.

A 96 well Immulon-2 microtiter plate (Dynatech-Immulon) is coated with 50 μl/well of RGD-affinity purified GPIIb/IIIa (effective range 0.5–10 μg/mL) in 10 mM HEPES, 150 mM NaCl, 1 mM at pH 7.4. The plate is covered and incubated overnight at 4° C. The GPIIb/IIa solution is discarded and 150 μl of 5% BSA is added and incubated at RT for 1–3 h. The plate is washed extensively with modified Tyrodes buffer. Biotinylated fibrinogen (25 μl/well) at 2× final concentration is added to the wells that contain the test compounds (25 μl/well) at 2× final concentration. The plate is covered and incubated at RT for 2–4 h. Twenty minutes prior to incubation completion, one drop of Reagent A (Vecta Stain ABC Horse Radish Peroxidase kit, Vector Laboratories, Inc.) and one drop Reagent B are added with mixing to 5 mL modified Tyrodes buffer mix and let stand. The ligand solution is discarded and the plate washed (5×200 μl/well) with modified Tyrodes buffer. Vecta Stain HRP-Biotin-Avidin reagent (50 μl/well, as prepared above) is added and incubated at RT for 15 min. The Vecta Stain solution is discarded and the wells washed (5×200 μl/well) with modified Tyrodes buffer. Developing buffer (10 mL of 50 mM citrate/phosphate buffer @ pH 5.3, 6 mg o-phenylenediamine, 6 μl 30% $H_2O_2$; 50 μl/well) is added and incubated at RT for 3–5 min, and then 2N $H_2SO_4$ (50 μl/well) is added. The absorbance is read at 490 nM. The results are shown in Table I.

IN VITRO INHIBITION OF THROMBIN-INDUCED GEL-FILTERED PLATELET AGGREGATION ASSAY.

The percentage of platelet aggregation is calculated as an increase in light transmission of compound treated platelet concentrate vs. control treated platelet concentrate. Blood is obtained from drug free, normal donors into tubes containing 0.13M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to $2 \times 10^7$ platelets per sample. The following constituents are added to a siliconized cuvette: concentrated platelet filtrate and Tyrode's buffer (0.1 4M NaCl, 0.0027M KCl, 0.01 2M $NaHCO_{3, 0.76}$ mM $Na_2HPO4$, 0.0055M glucose, 2 mg/mL BSA and 5.0 mM HEPES @ pH 7.4) in an amount equal to 350 μl, 50 μl of 20 mM calcium and 50 μl of the test compound. Aggregation is monitored in a BIODATA aggregometerforthe 3 min following the addition of agonist (thrombin 50 μl of 1 unit/mL). The results are shown in Table I.

EX VIVO DOG STUDY

Adult mongrel dogs (8–13 kg) were anesthetized with sodium pentobarbital (35 mg/kg, i.v.) and artificially respired. Arterial blood pressure and heart rate were measured using a Millar catheter-tip pressure transducer inserted in a femoral artery. Another Millar transducer was placed in the left ventricle (LV) via a carotid artery to measure LV end diastolic pressure and indices of myocardial contractility. A lead II electrocardiogram was recorded from limb electrodes. Catheters were placed in a femoral artery and vein to sample blood and infuse drugs, respectively. Responses were continuously monitored using a Modular Instruments data aquisition system.

Arterial blood samples (5–9 ml) were withdrawn into tubes containing 3.8% sodium citrate to prepare platelet rich plasma (PRP) and to determine effects on coagulation parameters: prothrombin time (PT) and activated partial thromboplastin time (APTT). Separate blood samples (1.5 ml) were withdrawn in EDTA to determine hematocrit and cell counts (platelets, RBC's and white cells). Template bleeding times were obtained from the buccal surface using a symplate incision devise and Whatman filter paper.

Aggregation of PRP was performed using a BioData aggregometer. Aggregation of whole blood used a Chronolog impedance aggregometer. PT and APTT were determined on either a BioData or ACL 3000+ coagulation analyser. Cells were counted with a Sysmex K-1000.

Compound 17 was solubilized in a small volume of dimethylformamide (DMF) and diluted with saline to a final concentration of 10% DMF. Compound 17 was administered by the intravenous route with a Harvard infusion pump. Doses of 0.3, 1, 3, and 10 mg/kg were given in a cumulative fashion to each animal. Each dose was administered over a 15 min interval at a constant rate of 0.33 ml/min. Data were obtained after each dose and 30 and 60 min following the end of drug administration.

Compound 17 caused marked inhibition of ex vivo platelet aggregation responses. Thus, in whole blood, Compound 17 inhibited collagen-stimulated aggregation in doses of 0.3–10 mg/kg with marked inhibition of collagen stimulated platelet ATP release at 10 mg/kg. In PRP, Compound 17 also inhibited collagen stimulated platelet aggregaton with marked activity at 0.3 mg/kg. Gamma thrombin induced aggregation of PRP was inhibited at doses of 3.0 mg/kg and above. In both PRP and whole blood, platelet function began to recover within 30–60 min, suggesting a relatively short duration of drug action. Compound 17 had no measurable hemodynamic effect in doses up to 10 mg/kg, iv. The drug produced an increase in template bleeding time at 3 and 10 mg/kg with rapid recovery post treatment. No effects on coagulation (PT or APTT) were observed during treatment and platelet, white and RBC counts were unchanged at any dose of Compound 17.

The results indicate that Compound 17 is a broadly effective inhibitor of platelet aggregation ex vivo (antagonizing both collagen and thrombin pathways) following iv adminnstration of doses ranging from 0.3–10 mg/kg. The antiaggregatory effect is relatively short and is accompanied by increases in bleeding time at the higher doses. No other hemodynamic or hematologic effects are observed.

TABLE I

| Compound # | Binding IC$_{50}$ ($\mu$M) | Pl. Aggr. @ 50 $\mu$M |
|---|---|---|
| 1 | 20.1 | 20% |
| 2 | 0.74 | 67% |
| 3 | 0.021 | 0.60 $\mu$M* |
| 4 | 2.6 | 21% |
| 5 | 0.013 | 1.6 $\mu$M* |
| 6 | 24% @ 50 $\mu$M | 4% |
| 7 | 0.074 | 86% |
| 8 | 2.7 | 28% |
| 9 | 59% @ 50 $\mu$M | 2% |
| 10 | 0.76 | 75% |
| 11 | 7.6 | 43% |
| 12 | 50 | 49% |
| 13 | 0.34 | 78% |
| 14 | 0.028 | 78% |
| 15 | 20% @ 5 $\mu$M | 4% |
| 16 | 0.008 | 73% |
| 17 | 0.003 | 0.13 $\mu$M* |
| 18 | 0.029 | 87% |
| 19 | 5.80 | 85% |

*Indicates IC$_{50}$

IN VIVO DOG STUDY

Compound 16 was tested in the following in vivo dog model to determine its therapeutic efficacy

Surgical Preparation

Adult mongrel dogs of either sex 9–13 kg) were anesthetized with pentobarbital sodium (35 mg/kg, i.v.) and ventilated with room air via an endotracheal tube (12 strokes/min, 25 ml/kg). For arterial pressure determination, the left carotid artery was cannulated with a saline-filled polyethylene catheter (PE-200) and connected to a Statham pressure transducer (P231D, Oxnard, Calif.). Mean arterial diastolic blood pressure. Heart rate was monitored using a cardiotachometer (Biotach, Gould Electronics, Cleveland, Ohio) triggered from a lead 11 electrocardiogram generated by limb leads. A jugular vein was cannulated (PE-200) for drug administration. The left femoral artery and the left femoral vein were cannulated with silicon treated (Sigmacote, Sigma Chemical Co., St. Louis, Mo.), saline filled polyethylene tubing (PE-200) and connected with a 5 cm section of silicon treated tubing (PE-240) to form an extracorporeal arteriovenous shunt (A-V). Shunt patency was monitored using a Doppler flow system (model VF-1, Crystal Biotech Inc., Hopkinton, Mass.) and proximal to the locus of the shunt. All parameters were monitored continuously on a polygraph recorder (Gould TA-4000, Oxnard Calif.) at a paper speed of 10 mm/min.

Protocol

On completion of a 15 min post surgical stabilization period, an occlusive thrombus was formed by the introduction of a thrombogenic surface (O braided silk thread, 5 cm in length, Ethicon Inc., Somerville, N.J.) into the shunt. Four consecutive 15 min shunt periods were employed with the first consisting of a vehicle infusion followed by increasing concentrations of Compound 16, SC-47643, saline with DMF or saline with citric acid administered as a bolus followed by an infusion beginning 5 min. before insertion of the thrombogenic surface and continued for an additional 15 min. AT the end of each 15 min shunt period the silk was carefully removed and weighed. A fifth shunt immediately following the total cumulative treatment dose was used to assess patency duration as indicated by time to total occlusion. Thrombus weight was calculated by subtracting the weight of the silk prior to placement from the total weight of the silk on removal from the shunt. Arterial blood was withdrawn prior to the first shunt and after each shunt period for determination of whole blood collagen-induced platelet aggregation, thrombin-induced platelet degranulation (platelet ATP release), prothrombin time and platelet count. Template bleeding time was performed beginning 10 min. into each shunt period.

Hematologic Studies

Platelet, WBC and RBC counts and hematocrit determinations were performed on whole blood collected in 2 mg/ml disodium EDTA using a Sysmex™ K1000 (Baxter Laboratories, McGraw Park, Ill.).

Whole blood platelet aggregation and ATP release were measured using a lumi-aggregation and ATP release were measured using a lumi-aggregometer (Chrono-log, Havertown, Pa.) by recording the change in impedance (platelet aggregation) and light transmission (ATP-release) through a stirred (1000 rpm) suspension of whole blood maintained at 37 C. Blood samples were collected in 0.01M of sodium citrate and diluted 50% with saline supplemented with 0.5 mM Ca (25 $\mu$l of 0.02M CaCl2 and 20 $\mu$l of luciferol (Chrono-log, Havertown, Pa.). Final volume was 1 ml. Aggregation was induced with collagen (2$\mu$g/ml) while in a separate sample, platelet degranulation was monitored using thrombin (0.5 U/ml) (Chrono-log, Havertown, Pa.) and the changes in impedance and luminescence recorded over 6 min. Prothrombin time (PT) was monitored using a microsample coagulation analyzer (Ciba Corning 512, Corning, N.Y.). Template bleeding time as performed by making an incision into the gum (Surgicutt, ITC Corp, Edison, N.J.) and the time to clot formation monitored.

Drugs

Compound 16;1+0.03, 3+0.1 and 5+0.3 mg/kg, i.v. (bolus)+mg/kg/hr,i.v. (infusion) was solubilized in saline+ DMF (5%) and serially diluted to achieve appropriate concentrations expressed as parent compound.

Statistical Analysis

The results are shown in Tables 2–4. All values are expressed as the mean and standard error of the mean. Statistical significance of the change was assessed based on change from baseline suing analysis of variance and Student's t-test. Differences were considered significant when $P<0.05$.

TABLE 2

Incidence of occlusive thrombus formation during treatment periods and post cumulative dose. The values given are the number of animals per group in which zero shunt blood flow has occurred and the shunt is no longer patent. Dogs are monitored for 60 min during the post treatment recovery period.

| Group | Period 1 Control Vehicle | Period 2 Treatment Dose 1 | Period 3 Treatment Dose 2 | Period 4 Treatment Dose 3 | Post Treatment |
|---|---|---|---|---|---|
| Control (DMF 5%) | 4/4 | 2/4 | 1/4 | 4/4 | 4/4 |
| CP #16 | 4/4 | 2/4 | 1/4 | 0/4 | 3/4 |
| Control (Citric Acid) | | 5/5 | 5/5 | 5/5 | 5/5 |

TABLE 3

Effect of Cmpd. #16, and on Thrombus Weight and Bleeding Time

| Treatment Group | N | Shunt Period | Thrombus Weight (mg) | Bleeding Time (seconds) |
|---|---|---|---|---|
| Control | 4 | Baseline | | 119 ± 18 |
| DMF 5% | 4 | 1 - Vehicle | 58 ± 5 | 116 ± 27 |
| | 4 | 2 - Dose 1 | 56 ± 5 | 120 ± 15 |
| | 4 | 3 - Dose 2 | 55 ± 6 | 104 ± 15 |
| | 4 | 4 - Dose 3 | 63 ± 5 | 121 ± 27 |
| Compound #16 | 4 | Baseline | | 101 ± 11 |
| | 4 | 1 - Vehicle | 68 ± 5 | 84 ± 8 |
| | 4 | 2 - Dose 1 | 52 ± 3 | 94 ± 7 |
| | 4 | 3 - Dose 2 | 27 ± 1* | 128 ± 14 |
| | 4 | 4 - Dose 3 | 19 ± 2* | 241 ± 23* |
| Control Citric Acid | 5 | Baseline | | 103 ± 14 |
| | 5 | 1 - Vehicle | 80 ± 5 | 80 ± 6 |
| | 5 | 2 - Dose 1 | 69 ± 4 | 88 ± 10 |
| | 5 | 3 - Dose 2 | 65 ± 7 | 93 ± 18 |

All values are expressed as mean ± SEM. All parameters were recorded immediately after each shunt period to assess treatment effects.
*Student's t-test vs pre-treatment, $P < 0.05$.

TABLE 4

Effect of Cmpd #16 on Platelet Count, Gamma Thrombin-Induced Platelet Aggregation, Collagen-Induced Platelet Aggregation, Blood Pressure and Heart Rate

| Treatment Group | N | Shunt Period | Platelet Count (× 1000 μl) | G-Thrombin-Induced Plat Agg (% inhib) | Collagen-Induced Plat Agg (% inhib) | Blood Pressure (mmHg) | Heart Rate (beat/min) |
|---|---|---|---|---|---|---|---|
| Control | 4 | Baseline | 299 ± 25 | | | 159 ± 5 | 168 ± 3 |
| DMF 5% | 4 | 1-Vehicle | 313 ± 20 | 6 ± 4 | 3 ± 3 | 159 ± 6 | 168 ± 3 |
| | 4 | 2-Dose 1 | 273 ± 23 | 7 ± 7 | 5 ± 5 | 162 ± 5 | 162 ± 5 |
| | 4 | 3-Dose 2 | 278 ± 35 | 8 ± 8 | 6 ± 6 | 169 ± 3 | 160 ± 7 |
| | 4 | 4-Dose 3 | 253 ± 15 | 4 ± 3 | 2 ± 2 | 163 ± 5 | 155 ± 2 |
| | 4 | 30 min post | 252 ± 32 | 5 ± 4 | 6 ± 4 | | |
| | 4 | 60 min post | 212 ± 43 | 7 ± 3 | 6 ± 4 | | |
| Cmpd #16 | 4 | Baseline | 409 ± 27 | | | 137 ± 13 | 141 ± 7 |
| | 4 | 1-Vehicle | 380 ± 26 | 9 ± 6 | 9 ± 9 | 141 ± 11 | 143 ± 6 |
| | 4 | 2-Dose 1 | 352 ± 20 | 8 ± 5 | 14 ± 3 | 147 ± 8 | 146 ± 6 |
| | 4 | 3-Dose 2 | 353 ± 22 | 34 ± 8* | 99 ± 1* | 141 ± 10 | 138 ± 4 |
| | 4 | 4-Dose 3 | 358 ± 26 | 72 ± 8* | 100 ± 0* | 141 ± 9 | 136 ± 7 |
| | 4 | 30 min post | 339 ± 25 | 21 ± 8 | 82 ± 13* | | |
| | 4 | 60 min post | 360 ± 22 | 11 ± 5 | 57 ± 14* | | |
| Control Citric Acid | 5 | Baseline | 317 ± 36 | not done | | 133 ± 9 | 154 ± 9 |
| | 5 | 1-Vehicle | 315 ± 35 | | 5 ± 3 | 133 ± 9 | 154 ± 9 |
| | 5 | 2-Dose 1 | 313 ± 34 | | 0 ± 8 | 131 ± 8 | 152 ± 8 |
| | 5 | 3-Dose 2 | 313 ± 44 | | 18 ± 5 | 133 ± 8 | 151 ± 11 |

All values are expressed as mean ± SEM. All parameters were recorded immediately after each shunt period to assess treatment effects.
*Student's t-test vs pre-treatment, $P < 0.05$.

EXAMPLES

Protected amino acids were purchased from Bachem Bioscience Inc. Use of protected amino N-hydroxysuccinimide esters precludes the use of BOP-Cl (see synthesis of compound 14). Enantiomerically-enriched nipecotic acid methyl esters were isolated by chiral resolution of racemic material as published (A. M. Akkerman, *Rec. Trav. Chim. Pays-Bas* 1951, 70, 899). All other chemicals were purchased from Aldrich Chemical Company, Inc. High field $^1$H NMR spectra were recorded on a Bruker AC-360 spectrometer at 360 MHz, and coupling constants are given in Herz. Melting points were determined on a Mel-Temp II melting point apparatus and are uncorrected. Microanalyses were performed at Robertson Microlit Laboratories, Inc., Madison, N.J. or The R. W. Johnson Pharmaceutical Research Institute Analytical Department. Final compounds were purified by recrystallization/precipitation from common organic solvents and/or column chromatography using Merck silica gel-60. Purities were assessed on a combination Beckman/Waters HPLC System and a Phenomenex-Ultracarb 5 ODS(30) column (100×4.6 mm) using an aqueous acetonitrile mobile phase (typically 10% MeCN/90% water). In the Examples and throughout this application, the following abbreviations have the meanings recited hereinafter.

Ac=Acetyl

Bn or Bzl=Benzyl

Boc=t-Butoxycarbonyl

BOP-Cl=Bis(2-oxo-3-oxazolidinyl)phosphinic chloride

Cbz=Benzyloxycarbonyl

CP=compound

DiBAL=Diisobutylaluminum hydride

EDC=Ethyl dimethylaminopropylcarbodiimide

EDTA=Ethylenediaminetetraacetic acid

HOBT=Hydroxybenzotriazole i-Pr=Isopropyl

NMM=N-Methylmorpholine

Nip=Nipecotyl (Unless noted otherwise, racemic at 3-position)

PTSA=p-Toluenesulfonic acid

RT=room temperature

TFA=Trifluoroacetic acid

EXAMPLE 1

Nα-Boc-D-Lys-S-(+)-Nip-γ-Ala-OH (CP #14)

To a mixture of Nα-Boc-D-Lys(Cbz)-OH (2.9 g, 7.74 mmol) and $CH_2Cl_2$ (80 mL) at 50°C. was added BOP-Cl (1.96 g, 7.7 mmol) and NMM (0.83 mL, 7.7 mmol). This mixture was stirred for 30 min, treated with S-(+)-nipecotic acid methyl ester hydrochloride (1.39 g, 7.7 mmol) and NMM (0.83 mL), stirred for 2 h at 50°C., and diluted with sat'd $NH_4Cl$ (50 mL). The organic layer was separated from the aqueous layer, dried with MgSO4, and evaporated to a glassy solid. This solid was purified by flash chromatography (4% EtOH/CH$_2$Cl$_2$) to afford Nα-Boc-D-Lys(Cbz)-S-(+)-Nip-OMe as a white foam: $^1$ H NMR (CDCl$_3$)δ 7.30 (m, 5 H), 5.50 (m, 1 H), 5.09 (s, 2 H), 4.61 (m, 1 H), 3.92 (m, 1 H), 3.66 (s, 3 H), 3.20 (m, 4 H), 2.79 (m, 1 H), 2.51 (m, 1 H), 2.12 (m, 1 H), 1.50–1.80 (m, 10 H), 1.39 (s, 9 H); MS m/e 506 (MH+).

To a solution of Nα-Boc-D-Lys(Cbz)-S-(+)-Nip-OMe (3.52 g, 7.0 mmol) in THF (25 mL) at RT was added aqueous lithium hydroxide (0.19 g in 15 mL water) dropwise over a 3 min period. This solution was stirred for 6 h and evaporated to give a white foam. This foam was slurried with CH$_2$Cl$_2$ (80 mL) at RT and treated sequentially with H-β-Ala-OBn.PTSA (2.43 g, 7.0 mmol), HOBT (5 mg), EDC.HCl (1.98 g, 10.4 mmol), and NMM (0.76 mL, 7.0 mmol). This mixture was stirred for 13 h, diluted with sat'd NH$_4$Cl (50 mL), and the layers separated. The organic layer was dried with MgSO$_4$ and evaporated to give a white foam. The foam was purified by flash chromatography (3–4% EtOH/CH$_2$Cl$_2$) to give Nα-Boc-D-Lys(Cbz)-S-(+)-Nip-γ-Ala-OBn as a white foam: $^1$H NMR (CDCl$_3$)δ 7.35 (m, 10 H), 6.29 (m, 1 H), 5.45 (m, 1 H), 5.12 (s, 2 H), 5.05 (s, 2 H), 5.00 (m, 1 H), 4.55 (m, 1 H), 4.32 (m, 1 H), 3.48 (m, 2 H), 3.19 (m, 4 H), 2.53 (m, 3 H), 2.21 (m, 1 H), 1.84 (m, 1 H), 1.48–1.72 (m, 9 H), 1.42 (s, 9 H); MS m/e 653 (MH+).

To a solution of Nα-Boc-D-Lys(Cbz)-S-(+)-Nip-γ-Ala-OBn (0.80 g, 1.22 mmol) in THF (15 mL) in a Parr bottle under nitrogen atmosphere was added AcOH (5 mL), water (10 mL), and Pd/C (10%, 0.09 g). This mixture was hydrogenated at 50 psi/RT for 21 h, filtered through Celite, and evaporated to ca. 5 mL. This solution was treated with Et$_2$O (60 mL) to give a white ppt which was filtered and lyophilized to afford 14 as colorless flakes: mp 52°–60° C.; $^1$H NMR (DMSO-d$_6$)γ 7.85 (m, 1 H), 6.83 (d, J=7, 1 H), 4.34 (d, J=12, 1 H), 4.22 (m, 1 H), 3.60 (m, 2 H), 3.41 (m, 2 H), 2.98 (t, J=11, 1 H), 2.88 (m, 1 H), 2.69 (m, 2 H), 2.35 (m, 2 H), 2.12 (m, 1 H), 2.03 (m, 1 H), 1.70 (m, 2 H), 1.4–1.6 (m, 8 H), 1.35 and 1.38 (pr. s, 8.5:1, 9 H), 1.16 (m, 2 H); IR (KBr) 3450-2860, 1709, 1641 cm$^{-1}$; MS m/e 429 (MH+); [α]$^{25}$D −15.20°(c 0.63, MeOH). Anal. calcd. for C$_{20}$H$_{36}$N$_4$O$_6$.C$_2$H$_4$O$_2$ (488.6): C, 54.08; H, 8.25; N, 11.47. Found: C, 54.64; H, 8.26; N, 10.79.

EXAMPLE 2

Nα-Boc-L-Lys(Cbz)-Nip-Ala-OBn (CP #1)

Compound 1, prepared starting from Nα-Boc-L-Lys(Cbz)-OH and racemic nipecotic acid methyl ester, as in Example 1, was isolated as a glass: $^1$ H NMR (CDCl$_3$)δ 7.29 (m, 10 H), 6.51 (m, 1 H), 5.39 (m, 1 H), 5.11 (s, 2 H), 5.06 (s, 2 H), 4.94 (m, 1 H), 4.54 (m, 2 H), 4.18 (m, 1 H), 4.02 (d, J=10, 1 H), 3.61 (m, 1 H), 3.48 (m, 2 H), 3.17 (m, 4 H), 2.54 (m, 3 H), 2.20 (m, 1 H), 1.83 (m, 1 H), 1.67 (m, 2 H), 1.51 (m, 4 H), 1.39 (s, 9 H); MS m/e 653 (MH+); Anal. calcd. for C$_{35}$H$_{48}$N$_4$O$_8$.5H$_2$O (679.8): C, 61.84; H, 7.56; N, 8.24. Found: C, 62.00; H, 7.25; N, 8.23.

EXAMPLE 3

Nα-Boc-L-Lys-Nip-γ-Ala—OH (CP #2)

Compound 2, prepared by hydrogenolysis of 1, as in Example 1, was isolated as a white foam: $^1$ H NMR (DMSO-d$_6$)γ 8.00 (m, 1 H), 7.86 (m, 1 H), 4.29 (m, 2 H), 3.82 (m, 1 H), 3.11 (m, 3 H), 2.70 (m, 2 H), 2.53 (m, 1 H), 2.31 (m, 2 H), 2.17 (m, 1 H), 1.4–1.9 (m, 10 H), 1.34 and 1.36 (pr. s,1:1, 9 H), 1.23 (m, 2 H); MS m/e 429 (MH+); [α]$^{25}$D+0.85° (c 0.82, MeOH). Anal. calcd. for C$_{20}$H$_{36}$N$_4$O$_6$.1.5H$_2$O (518.6): C, 53.27; H, 8.16; N, 10.80. Found: C, 53.61; H, 8.18; N, 10.47.

EXAMPLE 4

Nα-Boc-D-Lys-Nip-γ-Ala—OH (CP #3)

Nα-Boc-D-Lys(Cbz)-Nip-γ-Ala-OBn, prepared starting from racemic nipecotic acid methyl ester and Nα-Boc-D-Lys(Cbz)-OH, as in Example 1, was isolated as a white foam: $^1$ H NMR (CDCl$_3$)γ 7.32 (m, 10 H), 6.59 (m, 1 H), 5.45 (m, 1 H), 5.12 (s, 2 H), 5.07 (s, 2 H), 4.94 (m, 1 H), 4.56 (m, 1 H), 4.12 (m, 1 H), 3.51 (m, 2 H), 3.17 (m, 3 H), 2.57 (m, 2 H), 2.21 (m, 1 H), 1.89 (m, 1 H), 1.45–1.79 (m, 11 H), 1.41 (s, 9 H); MS m/e 653 (MH+).

Compound 3, prepared by hydrogenolysis of Nα-Boc-D-Lys(Cbz)-Nip-γ-Ala-OBn, as in Example 1, was isolated as colorless flakes: mp 48°–54° C.; $^1$ H NMR (DMSO-d$_6$)γ 7.96 (m, 1 H), 6.82 (m, 1 H), 4.30 (m, 2 H), 3.81 (m, 1 H), 3.12 (m, 4 H), 2.69 (m, 2 H), 2.56 (m, 1 H), 2.33 (m, 2 H), 2.14 (m, 2 H), 1.80 (m, 2 H), 1.4–1.7 (m, 9 H), 1.32 and 1.34 (pr. s, 1:1, 9 H), 1.22 (m, 2 H); IR (KBr) 3580-2770, 1711, 1642 cm$^{-1}$; MS m/e 429 (MH+); [α]$^{25}$D −7.78°(c 1.71, MeOH). Anal. calcd. for C$_{20}$H$_{36}$N$_4$O$_6$.2C$_2$H$_4$O$_2$.0.5H$_2$O (557.6): C, 51.69; H, 8.13; N, 10.05. Found: C, 51.46; H, 8.11; N, 10.10.

EXAMPLE 5

Nα-Boc-D-Lys-Nip-L-Asp-OMe (CP #18).

Nα-Boc-D-Lys(Cbz)-Nip-L-Asp(OBn)-OMe, prepared from H-L-Asp(OBn)-OMe and Nα-Boc-D-Lys(Cbz)-Nip-OH, as in Example 1, was isolated as a glass: $^1$H NMR (CDCl$_3$)γ 7.36 (m, 10 H), 6.84 (m, 1 H), 5.40 (m, 1 H), 5.14 (s, 2 H), 5.09 (s, 2 H), 4.88 (m, 2 H), 4.54 (m, 1 H), 4.30 (m, 1 H), 3.68 (s, 3 H) 3.19 (m, 3 H) 3.03 (m, 1 H), 2.89 (m, 1 H), 2.29 (m, 1 H), 1.43-2.06 (m, 12 H), 1.40 (s, 9 H); MS m/e 711 (MH+).

Compound 18, prepared by hydrogenolysis of Nα-Boc-D-Lys(Cbz)-Nip-L-Asp(OBn)-OMe, as in Example 1, was isolated as white foam:$^1$H NMR (DMSO-d$_6$)γ 8.33 (m, 1 H), 6.77 (d, J=7, 1 H), 4.32 (m, 3 H), 3.82 (m, 1 H), 3.59 (s, 3 H), 2.96 (m, 2 H), 2.73 (m, 3 H), 2.46 (m, 2 H), 2.34 (m, 1 H), 1.79 (m, 3 H), 1.4–1.7 (m, 8 H), 1.34 and 1.37 (pr. s, 1:1, 9 H), 1.27 (m, 2 H); MS m/e 487 (MH+); [α]$^{25}$D −3.57° (c 0.56, MeOH). Anal. calcd. for C$_{22}$H$_{38}$N$_4$O$_8$.C$_2$H$_4$O$_2$.H$_2$O (564.6): C, 51.05; H, 7.85; N, 9.92. Found: C, 50.89; H, 7.88; N, 9.74.

EXAMPLE 6

H-L-Lys-Nip-γ-Ala-OH (CP #4)

To a solution of compound 2 (0.30 g, 0.70 mmol) in MeOH (10 mL) and water (10 mL) at RT was added HCl (0.50 mL, conc.). This solution was stirred for 1 h and evaporated to ca. 2 mL oil. This oil was treated with MeCN (20 mL), filtered, washed with Et$_2$O (3×20 mL), and dried to afford 4 as a white powder: mp 65°–75° C.; $^1$H NMR (DMSO-d$_6$)γ 8.23 (m, 3 H), 8.06 (m, 3 H), 4.33 (m, 2 H), 3.73 (m, 4 H), 3.25 (m, 2 H), 3.01 (m, 1 H), 2.72 (m, 2 H), 2.44 (m, 1 H), 2.34 (m, 2 H), 1.5–1.8 (m, 6 H), 1.35 (m, 4 H); MS m/e 329 (MH+); Anal. calcd. for C$_{15}$H$_{28}$N$_4$O$_4$.2HCl.2H$_2$O (437.4): C, 41.19; H, 7.84; N, 12.81. Found: C, 40.97; H, 7.75; N, 12.44.

EXAMPLE 7

N-(Nε- nocaroyl)-Nip-β-Ala-OH (CP #5)

N-(Nε-Boc-aminocaproyl)-Nip-β-Ala-OBn, prepared starting from racemic nipecotic acid methyl ester and Nε-Boc-aminocaproic acid N-oxysuccinimide ester, as in Example 1, was isolated as an oily solid: $^1$H NMR (CDCl$_3$)δ 7.34 (m, 5 H), 6.51 (m, 1 H), 5.12 (s, 2 H), 4.60 (m, 1 H), 4.39 (m, 1 H), 3.90 (m, 1 H), 3.71 (t, 1 H), 3.52 (m, 3 H), 3.19 (m, 4 H), 2.59 (m, 2 H), 2.30 (m, 2 H), 1.85 (m, 3 H), 1.63 (m, 2 H), 1.51 (m, 2 H), 1.42 (s, 9 H), 1.34 (m, 2 H); MS m/e 504 (MH+).

Compound 5, prepared by hydrogenolysis and then acid hydrolysis of N-(Nε-Boc-aminocaproyl)-Nip-⊖-Ala-OBn, as in Example 1, was isolated as a glass: $^1$H NMR (DMSO-d$_6$)γ 8.18 (t, J=5, 1 H), 8.04 (br. s, 3 H), 4.28 (m, 2 H), 3.78 (m, 2 H), 3.20 (m, 3 H), 2.99 (t, J=12, 1 H), 2.71 (d, J=6, 2 H), 2.39 (m, 2 H), 2.31 (m, 2 H), 2.16 (m, 1 H), 1.79 (m, 1 H), 1.61 (m, 4 H), 1.42 (t, J=6, 2 H), 1.28 (m, 2 H), 1.19 (m, 1 H); MS m/e 314 (MH+); Anal. calcd. for C$_{15}$H$_{27}$N$_3$O$_4$.2HCl (386.3): C, 46.04; H, 7.57; N, 10.88. Found: C, 45.91; H, 7.63; N, 11.17.

EXAMPLE 8

N-[3-(4-Piperidinepropionyl)]-Nip-β-Ala-OH (CP #17)

N-[3-(4-Pyridineacryloyl)]-Nip-β-Ala-OBn, prepared starting from 3-(4-pyridine)acrylic acid and racemic nipecotic acid methyl ester, as in Example 1, was isolated as a glass: $^1$H NMR (CDCl$_3$)γ 8.61 (d, J=4 Hz, 2 H), 7.52 (d, J=15 Hz, 1 H), 7.35 (m, 7 H) 7.03 (d, J=15 Hz, 1 H), 6.58 (m, 1 H), 5.12 (s, 2 H), 4.40 (m, 1 H), 3.89 (m, 1 H), 3.51 (m, 2 H), 3.38 (m, 2 H), 2.60 (t, J=6 Hz, 2 H), 2.31 (m, 1 H), 1.97 (m, 2 H), 1.74 (m, 1 H), 1.56 (m, 1 H); MS m/e 422 (MH+).

To a solution of N-[3-(4-Pyridineacryloyl)]-Nip-β-Ala-OBn (0.56 g, 1.33 mmol) in EtOH (20 mL) and water (10 mL) under nitrogen atmosphere was added HCl (0.66 mL, 4.0M in dioxane) and platinum$^{IV}$ oxide (0.060 g). This mixture was hydrogenated at 50 psi/RT for 22 h, filtered through Celite, and evaporated to ca. 5 mL. This solution was treated with MeCN (30 mL), filtered, washed with Et$_2$O (3×20 mL), and dried to give 17 as a pale yellow foam: $^1$H NMR (DMSO-d$_6$)δ 9.02 (br. s, 2 H), 8.03 (m, 1 H), 7.46 (m, 1 H), 4.28 (t, J=7, 1 H), 4.11 (m, 1 H), 3.79 (m, 1 H), 3.44 (t, J=7, 1 H), 3.19 (m, 3 H), 3.06 (t, J=12, 1 H), 2.75 (d, J=11, 1 H), 2.53 (m, 1 H), 2.32 (m, 4 H), 2.12 (m, 1 H), 1.77 (m, 2 H), 1.4–1.7 (m, 7 H), 1.27 (m, 2 H), 1.18 (t, J=6, 1 H); MS m/e 340 (MH+); Anal. calcd. for C$_{17}$H$_{29}$N$_3$O$_4$.2HCl (412.4): C, 49.52; H, 7.58; N, 10.19. Found: C, 49.15; H, 7.02; N, 10.48. Accurate protonated mass calcd. for C$_{17}$H$_{29}$N$_3$O$_4$: 340.2236 amu. Found: 340.2245 amu.

EXAMPLE 9

Nα-Ac-L-Lys-Nip-Gly-OH (CP #6)

Nα-Ac-L-Lys(Boc)-Nip-Gly-OBn, prepared starting from Nα-Ac-L-Lys(Boc)-OH and racemic nipecotic acid methyl ester (see 14), was isolated as a glass: $^1$H NMR (CDCl$_3$)δ 7.35 (m, 5 H), 6.97 (m, 1 H), 6.38 (m, 1 H), 5.14 (s, 2 H), 4.70 (m, 1 H), 4.46 (m, 1 H), 4.06 (dd, J=5, 16 Hz, 2 H), 3.71 (m, 1 H), 3.10 (m, 2 H), 1.99 (s, 3 H), 1.91 (m, 2 H), 1.64 (m, 1 H), 1.41–1.60 (m, 1 H), 1.39 (s, 9 H); MS m/e 547 (MH+).

Compound 6, prepared by hydrogenolysis of Nα-Ac-L-Lys(Boc)-Nip-Gly-OBn, as in Example 1, and then TFA-mediated Boc removal (for method, see M. Bodanszky The Practice of Peptide Synthesis, Springer-Verlag: New York, 1984), was isolated as atan powder: mp 40°–55° C.; $^1$H NMR (DMSO-d$_6$)δ 8.24 (t, J=6, 1 H), 8.03 (d, J=8, 1 H), 7.75 (br. s, 3 H), 4.24 (m, 1 H), 3.72 (t, J=6, 2 H), 3.61 (m, 2 H), 2.72 (m, 2 H), 1.83 (s, 3 H), 1.78 (m, 2 H), 1.63 (m, 2 H), 1.4-1.6 (m, 8 H), 1.28 (m, 4 H); MS mle 357 (MH+); Anal. calcd. for C$_{16}$H$_{28}$N$_4$O$_5$3C$_2$HF$_3$O$_2$ (698.5): C, 37.83; H, 4.47; N, 8.02. Found: C, 37.91; H, 4.89; N, 8.47.

EXAMPLE 10

Nα-Ac-L-Lys-Nip-β-Ala-OH (CP #7)

Nα-Ac-L-Lys(Boc)-Nip-β-Ala-OBn, prepared starting from Nα-Ac-L-Lys(Boc)-OH and racemic nipecotic acid methyl ester as, in Example 1, was isolated as a white foam: $^1$H NMR (CDCl$_3$)δ 7.34 (m, 5 H), 6.53 (m, 2 H), 5.12 (s, 2 H), 4.58 (m, 1 H), 4.10 (m, 1 H), 3.72 (m, 1 H), 3.54 (m, 2 H), 3.11 (m, 3 H), 2.59 (m, 2 H), 2.24 (m, 1 H), 2.01 (s, 3 H), 1.88 (m, 1 H), 1.73 (m, 2 H), 1.52 (m, 8 H), 1.40 (s, 9 H), 1.31 (m, 1 H); MS m/e 561 (MH+).

Compound 7, prepared by hydrogenolysis of Nα-Ac-L-Lys(Boc)-Nip-β-Ala-OBn, as in Example 1, and then acid hydrolysis, as in Example 6, was isolated as a white foam: mp 53°–67° C.; $^1$H NMR (DMSO-d$_6$)δ 8.13 (m, 1 H), 8.00 (m, 1 H), 7.91 (d, J=15, 3 H), 4.64 (m, 1 H), 4.36 (m, 1 H), 3.87 (m, 1 H), 3.66 (m, 2 H), 3.23 (m, 3 H), 2.99 (m, 1 H), 2.68 (m, 2 H), 2.59 (m, 1 H), 2.38 (m, 2 H), 2.11 (m, 1 H), 1.80 (s, 3 H), 1.63 (m, 1 H), 1.4-1.6 (m, 5 H), 1.24 (m, 3 H); MS m/e 371 (MH+); Anal. calcd. for C$_{17}$H$_{30}$N$_4$O$_5$.2HCl.2H$_2$O (479.4): C, 42.59; H, 7.57; N, 11.69. Found: C, 43.83; H, 7.79; N, 10.91.

EXAMPLE 11

Nα-Boc-L-Arg-Nip-β-Ala-OH (CP #8)

Nα-Boc-L-Arg(Cbz)-Nip-β-Ala-OBn, prepared starting from Nα-Boc-L-Arg(Cbz$_2$)-OSu and racemic nipecotic acid methyl ester, as in Example 1, was isolated as a glass: $^1$H NMR (CDCl$_3$)δ 7.33 (m, 10 H), 6.69 (m, 1 H), 5.70 (m, 1 H), 5.13 (s, 2 H), 5.03 (s, 2 H), 4.59 (m, 1 H), 4.29 (m, 1 H), 3.52 (m, 2 H), 3.28 (m, 1 H), 3.09 (m, 3 H), 2.60 (m, 3 H), 2.18 (m, 1 H), 1.49–1.90 (m, 11 H), 1.42 (s, 9 H); MS m/e 681 (MH+).

Compound 8, prepared by hydrogenolysis of Nα-Boc-L-Arg(Cbz)-Nip-β-Ala-OBn, as in Example 1, was isolated as a white foam: mp 47°–55° C.; $^1$H NMR (DMSO-d$_6$)γ 9.53 (m, 1 H), 7.85 (m, 2 H), 6.96 (m, 1 H), 4.32 (m, 2 H), 3.84 (m, 1 H), 3.38 (m, 2 H), 3.03 (m, 4 H), 2.20 (m, 3 H), 1.74 (m, 2 H), 1.4–1.7 (m, 8 H), 1.35 (s, 9 H), 1.24 (m, 2 H); MS mle 457 (MH+); Anal. calcd. for C$_{20}$H$_{36}$N$_6$O$_6$.1.5C$_2$H$_4$O$_2$ (546.6): C, 50.54; H, 7.74; N, 15.37. Found: C, 50.24; H, 7.96; N, 15.26.

EXAMPLE 12

Nα-Boc-L-Lys-Nip-γ-aminobutyric acid (CP #9)

Nα-Boc-L-Lys(Cbz)-Nip-γ- aminobutyric acid benzyl ester, prepared starting from Nα-Boc-L-Lys(Cbz)-OH and racemic nipecotic acid methyl ester (see I-1, I-2), was isolated as a glass: $^1$H NMR (CDCl$_3$)δ 7.33 (m, 10 H), 6.48 (m, 1 H), 6.16 (m, 1 H), 5.40 (m, 1 H), 5.11 (s, 2 H), 5.08 (s, 2 H), 4.89 (m, 1 H), 4.58 (m, 1 H), 4.07 (m, 1 H), 3.22 (m, 5 H), 2.52 (m, 1 H), 2.40 (m, 2 H), 1.50–2.30 (m, 12 H), 1.42 (s, 9 H), 1.33 (m, 1 H); MS m/e 667 (MH+).

Compound 9, prepared by hydrogenolysis of Nα-Boc-L-Lys(Cbz)-Nip-γ-aminobutyric acid benzyl ester, as in Example 1, was isolated as a white foam: mp 65°–71° C.; $^1$H NMR (DMSO-d$_6$)γ 8.25 (m, 1 H), 6.87 (m, 1 H), 4.31 (m, 3 H), 3.74 (m, 2 H), 3.15 (m, 2 H), 2.98 (m, 3 H), 2.69 (m, 2 H), 2.10 (m, 3 H), 1.76 (m, 3 H), 1.4–1.7 (m, 9 H), 1.31 (s, 9 H), 1.21 (m, 2 H); MS m/e 443 (MH+); Anal. calcd. for $C_{21}H_{38}N_4O_6 \cdot 2C_2H_4O_2$ (562.7): C, 53.37; H, 8.24; N, 9.96. Found: C, 53.94; H, 8.17; N, 9.70.

EXAMPLE 13

H-D-Lys-Nip-β-Ala-OH (CP #10)

Compound 10, prepared by acid hydrolysis of 3, as in Example 6, was isolated as a cream powder: mp 108°–128° C.; 1H NMR (DMSO-$d_6$)δ 8.28 (m, 3 H), 8.05 (m, 3 H), 4.31 (m, 2 H), 3.84 (m, 2 H), 3.25 (m, 2 H), 3.09 (m, 2 H), 2.72 (m, 3 H), 2.37 (m, 3 H), 1.80 (m, 1 H), 1.5-1.7 (m, 6 H), 1.33 (m, 4 H); MS m/e 329(MH+); Anal. calcd. for $C_{15}H_{28}N_4O_4 \cdot 2HCl \cdot C_2H_4O_2$ (461.4): C, 44.26; H, 7.43; N, 12.14. Found: C, 43.98; H, 7.27; N, 12.29.

EXAMPLE 14

Nα-Boc-D-Lys-Nip-γ-aminobutyric acid (CP #11)

Nα-Boc-D-Lys(Cbz)-Nip-γ-aminobutyric acid benzyl ester, prepared starting from Nα-Boc-D-Lys(Cbz)-OH and racemic nipecotic acid methyl ester, as in Example 1, was isolated as a glass: $^1$H NMR (CDCl$_3$)δ 7.31 (m, 10 H), 6.51 (m,1 H), 6.15 (m, 1 H), 5.48 (m, 1 H), 5.10 (s, 1 H), 5.06 (s, 2 H), 4.90 (m, 1 H), 4.55 (m, 1 H), 4.10 (m, 1 H), 3.59 (m, 1 H), 3.23 (m, 5 H), 2.39 (m, 2 H), 2.23 (m, 1 H), 1.84 (m, 2 H), 1.45–1.80 (m, 10 H), 1.38 (s, 9 H), 1.32 (m, 1 H); MS m/e 667 (MH+).

Compound 11, prepared by hydrogenolysis of Nα-Boc-D-Lys(Cbz)-Nip-γ-aminobutyric acid benzyl ester, as in Example 1, was isolated as a tan powder: mp 50–57° C.; $^1$H NMR (DMSO-$d_6$)δ 7.97 (m, 1 H), 6.91 (m, 1 H), 4.32 (m, 1 H), 4.22 (m, 1 H), 3.82 (m, 1 H), 3.02 (m, 3 H), 2.71 (m, 2 H), 2.52 (m, 1 H), 2.29 (m, 1 H), 2.17 (m, 2 H), 1.84 (m, 5 H), 1.4–1.7 (m, 9 H), 1.33 (s, 9 H), 1.19 (m, 2 H); MS m/e 443 (MH+); Anal. calcd. for $C_{21}H_{38}N_4O_6 \cdot C_2H_4O_2 \cdot 0.5H_2O$ (571.7): C, 52.53; H, 8.29; N, 9.80. Found: C, 52.91; H, 8.21; N, 9.39.

EXAMPLE 15

Nα-Boc-D-Lys-Nip-Gly-OH (CP #1 2)

Nα-Boc-D-Lys(Cbz)-Nip-Gly-OBn, prepared starting from Nα-Boc-D-Lys(Cbz)-OH and racemic nipecotic acid methyl ester, as in Example 1, was isolated as a glass: $^1$H NMR (CDCl$_3$)δ 7.39 (m, 10 H), 6.87 (m, 1 H), 5.42 (m, 1 H), 5.19 (s, 2 H), 5.13 (s, 2 H), 4.93 (m, 1 H), 4.60 (m, 1 H), 4.20 (m, 1 H), 4.09 (m, 1 H), 3.40–4.00 (m, 3 H), 3.21 (m, 2 H), 2.61 (m, 1 H), 2.43 (m, 1 H), 1.45–2.20 (m, 10 H), 1.39 (s, 9 H); MS m/e 639 (MH+).

Compound 12, prepared by hydrogenolysis of Nα-Boc-D-Lys(Cbz)-Nip-Gly-OBn, as in Example 1, was isolated as white flakes: mp 66°–80° C.; $^1$H NMR (DMSO-$d_6$)δ 7.82 (m, 1 H), 6.81 (d, J=7, 1 H), 4.34 (m, 2 H), 4.09 (m, 1 H), 3.77 (m, 1 H), 3.48 (m, 1 H), 3.16 (m, 2 H), 2.70 (m, 3 H), 2.44 (m, 2 H), 2.28 (m, 1 H), 1.78 (m, 2 H), 1.4–1.7 (m, 8 H), 1.32 and 1.35 (pr. s,1:1,9 H), 1.23 (m, 2 H); MS m/e 415 (MH+); Anal. calcd. for $C_{19}H_{34}N_4O_6 \cdot 2C_2H_4O_2$ (534.6): C, 51.67; H, 7.92; N, 10.48. Found: C, 52.06; H, 8.33; N, 10.19.

EXAMPLE 16

Nα-Ac-D s-Nip-β-Ala-OH (CP #13)

Nα-Ac-D-Lys(Cbz)-Nip-β-Ala-OBn , prepared starting from Nα-Ac-D-Lys(Cbz)-OH and racemic nipecotic acid methyl ester, as in Example 1, was isolated as a glass: $^1$H NMR (CDCl$_3$)δ 7.32 (m,10 H), 6.54 (m, 1 H), 6.36 (m, 1 H), 5.10 (s, 2 H), 5.02 (s, 2 H), 4.89 (m, 2 H), 4.48 (m, 1 H), 4.04 (m, 1 H), 3.69 (m, 1 H), 3.52 (m, 2 H), 3.17 (m, 3 H), 2.57 (m, 2 H), 2.20 (m, 1 H), 1.98 (s, 3 H), 1.25–1.90 (m, 10 H); MS mle 595 (MH+).

Compound 13, prepared by hydrogenolysis of Nα-Ac-D-Lys(Cbz)-Nip-β-Ala-OBn, as in Example 1, was isolated as a glass: mp 46°–59 C.; $^1$H NMR (DMSO-$d_6$)δ 8.11 (m, 3 H), 4.70 (m, 1 H), 4.33 (m, 1 H), 3.74 (m, 1 H), 3.38 (m, 1 H), 3.19 (m, 4 H), 3.00 (m, 1 H), 2.68 (m, 2 H), 2.21 (m, 4 H), 1.82 (s, 3 H), 1.76 (m, 2 H), 1.4–1.7 (m, 7 H), 1.24 (m, 2 H); MS m/e 371 (MH+); Anal. calcd. for $C_{17}H_{30}N_4O_5 \cdot 2.5C_2H_4O_2$ (520.6): C, 50.76; H, 7.74; N, 10.76. Found: C, 51.12; H, 8.04; N, 10.75.

EXAMPLE 17

Nα-Boc-L-Lys(i-Pr)-Nip-β-Ala-OH (CP #15)

Nα-Boc-L-Lys(i-Pr)(Cbz)-Nip-β-Ala-OBn , prepared starting from Nα-Boc-L-Lys(i-Pr)(Cbz)-OH and racemic nipecotic acid methyl ester, as in Example 1, was isolated as a glass: 1H NMR (CDCl$_3$)δ 7.33 (m, 10 H), 6.58 (m, 1 H), 5.10 (s, 2 H), 5.08 (s, 2 H), 4.55 (m, 1 H), 4.21 (m, 1 H), 3.73 (m, 1 H), 3.50 (m, 2 H), 3.17 (m, 3 H), 2.55 (m, 2 H), 2.18 (m, 1 H), 1.50-2.00 (m, 13 H), 1.40 (s, 9 H), 1.13 (d, J=8Hz, 6 H); MS m/e 695 (MH+).

Compound 15, prepared by hydrogenolysis of Nα-Boc-L-Lys(i-Pr)(Cbz)-Nip-β-Ala-OBn, as in Example 1, was isolated as white flakes: mp 90°–123° C.; $^1$H NMR (DMSO-$d_6$)δ 7.93 (m, 1 H), 6.81 (d, J=7, 1 H), 4.36 (m, 1 H), 4.24 (m, 1 H), 3.60 (m, 1 H), 3.37 (m, 1 H), 3.10 (m, 1 H), 2.91 (m, 3 H), 2.62 (m, 3 H), 2.39 (m, 2 H), 2.14 (m, 1 H), 2.05 (m, 1 H), 1.4–1.8 (m, 9 H), 1.34 and 1.37 (pr. s, 1:1, 9 H), 1.26 (m, 3 H), 1.13 (d, J=5, 6 H); IR (KBr) 3500-2830, 1704, 1638 cm$^{-1}$; MS m/e 471 (MH+); Anal. calcd. for $C_{23}H_{42}N_4O_6 \cdot 2C_2H_4O_2$ (590.7): C, 54.90; H, 8.53; N, 9.48. Found: C, 54.67; H, 8.65; N, 9.79.

EXAMPLE 18

Nα-Boc-D-Lys-R-(−)-Nip-β-Ala-OH (CP #16)

Compound 16, prepared starting from Nα-Boc-D-Lys (Cbz)-OH and R-(−)-nipecotic acid methyl ester, as in Example 1, was isolated as a colorless flakes: mp 42°–51° C.; $^1$H NMR (DMSO-$d_6$)δ 7.95 (m, 1 H), 6.82 (d, J=7, 1 H), 4.33 (m, 1 H), 4.19 (m, 1 H), 3.79 (m, 1 H), 3.25 (m, 1 H), 3.04 (t, J=10, 2 H), 2.69 (m, 2 H), 2.34 (m, 1 H), 2.21 (m, 1 H), 2.14 (m, 2 H), 1.78 (m, 2 H), 1.71 (m, 2 H), 1.4–1.6 (m, 9 H), 1.34 and 1.38 (pr. s,1:8, 9 H), 1.20 (m, 2 H); MS m/e 429 (MH+). Anal. calcd. for $C_{20}H_{36}N_4O_4 \cdot 2.5 C_2H_4O_2$ (578.7): C, 51.89; H, 8.01; N, 9.68. Found: C, 52.05; H, 7.98; N, 9.58.

EXAMPLE 19

N-(Nγ-Aminocaproyl)-3-piperidinemethylaminopropionic acid (CP #19)

To a solution of N-(Nε-Boc-aminocaproyl)-nipecotic acid (3.1 g, 9.0 mmol) and THF (50 mL) was added 1,1-carbonyidiimidazole (1.45 g, 9.0 mmol). This solution was stirred for 1 h, cooled to −10° C., treated with DiBAL (36.0 mL, 1.0M in toluene) dropwise over a 20 min period, and stirred for an additional 2 h. This solution was treated with aqueous citric acid (5.0 g in 40 mL water), diluted with CHCl$_3$ (200 mL), and the resultant layers were separated.

The aqueous layer was extracted with CHCl₃ (100 mL), and the combined organic layers were dried, evaporated, and purified by flash chromatography (4% EtOH/CH₂Cl₂) to afford N-(Nε-Boc-aminocaproyl)piperidine-3-carboxaldehyde as a glass: ¹H NMR (CDCl₃)δ 9.65 (d, J=8 Hz, 1 H), 4.58 (m, 1 H), 4.10 (m, 1 H), 3.65 (m, 1 H), 3.45 (m, 1 H), 3.22 (m, 1 H), 3.14 (m, 2 H), 2.46 (m, 2 H), 2.33 (t, J=7 Hz, 1 H), 2.09 (m, 1 H), 1.5–1.8 (m, 7 H), 1.39 (s, 9 H), 1.33 (m, 2 H); MS m/e 327 (MH+).

To a solution of N-(Nε-Boc-aminocaproyl)piperidine-3-carboxaldehyde (0.69 g, 2.12 mmol) in MeOH (10 mL) at RT was added H-β-Ala-OBn.PTSA (0.74 9, 2.12 mmol) and NaCNBH3 (0.13 g, 2.12 mmol). This mixture was stirred for 2.5 h and evaporated to a white solid. This solid was partitioned between sat'd NaHCO₃ (10 mL) and CH₂Cl₂ (50 mL), and the layers were separated. The aqueous layer was extracted with CH₂Cl₂ (2×50 mL), and the combined organic layers were dried, evaporated, and purified by flash chromatography (0.5% NH₄OH/4–10% EtOH/CH₂Cl₂) to give N-(Nε-Boc-aminocaproyl)-3-piperidinemethylaminopropionic acid benzyl ester as a glass: ¹H NMR (CDCl₃)δ 7.33 (m, 5 H), 5.13 (s, 2 H), 4.61 (m, 1 H), 4.28 (m, 1 H), 3.70 (m, 1 H), 3.11 (m, 3 H), 2.85 (m, 3 H), 2.53 (m, 4 H), 2.31 (t, J=7 Hz, 2 H), 1.5–1.9 (m, 8 H), 1.42 (s, 9 H), 1.29 (m, 3 H), 0.89 (m, 1 H); MS m/e 490 (MH+).

To a solution of N-(Nε-Boc-aminocaproyl)-3-piperidinemethylaminopropionic acid benzyl ester (0.28.g, 0.57 mmol) and THF (10 mL) at RT was added aqueous HCl (3.4 mL, 1.0N). This mixture was stirred for 22 h, evaporated to a glassy solid, triturated with Et₂O (3×25 mL), and dried to give a white powder. This powder was dissolved in THF (5 mL) and water (10 mL), transferred t a Parr bottle under nitrogen atmosphere, and treated with Pd/C (0.04 g, 10%). This mixture was hydrogenated at 50 psi/RT for 20 h, filtered 30 through Celite, and evaporated to ca. 5 mL. This solution was treated with MeCN (25 mL), filtered, washed with Et₂O (2×25 mL), and dried to give 19 as a colorless glass (HPLC purity>95%): mp 65°–74° C.; ¹H NMR (DMSO-d₆)δ 9.31 (m, 2 H), 8.12 (br. s,3 H), 4.18 (m, 2 H), 3.70 (m, 1 H), 3.04 (m, 2 H), 2.67 (m, 5 H), 2.51 (m, 1 H), 2.35 (m, 3 H), 1.87 (m, 2 H), 1.58 (m, 4 H), 1.42 35 (m, 2 H), 1.30 (m, 4 H); MS m/e 300 (MH+). Accurate protonated mass calcd. for $C_{15}H_{29}N_3O_3 \cdot 2HCl$ (372.3): 300.2287 amu. Found: 300.2306 amu.

---

---

We claim:

1. A compound represented by the general formula (I):

wherein $X^1$ and $X^2$ are the same or different and selected from either of $H_2$ or O;

wherein Y is selected from any of $(CH_2)m$, $CH(NHCOR^3)(CH_2)m$ or $CH((NH_2)CH_2)m$;

wherein A is a cycloalkyl ring containing a nitrogen therein which ring is selected from any of piperidin-2-yl, piperidin-3-yl, piperidin-4-yl, pyrrolidin-2-yl and pyrrolidin-3-yl;

wherein Z is selected from any of $(CH_2)n$ or $CH(CO_2R^4)(CH_2)n$;

wherein $R^2$ is selected from any of H or alkyl($C_1$–$C_8$);

wherein $R^3$ is selected from any of alkoxy ($C_1$–$C_8$) or alkyl ($C_1$–$C_8$);

wherein $R^4$ is alkyl ($C_1$–$C_8$) or arylalkyl ($C_1$–$C_8$);

wherein $R^6$ is H, alkyl ($C_1$–$C_8$) or arylalkyl ($C_1$–$C_8$);

wherein m is the integer 0, 1, 2, or 3;

wherein n is the integer 0, 1, or 2;

or the enantiomer or the pharmaceutically acceptable salt thereof.

2. The compound of claim 1, wherein Z is $(CH_2)_2$.
3. The compound of claim 1, wherein $R^2$ is H .
4. The compound of claim 1, whererin $R^3$ is t-butoxy.
5. The compound of claim 1, wherein $R^4$ is methyl.
6. The compound of claim 1, wherein Z is $CH(CO_2R^4)(CH_2)$.
7. The compound selected from any of:

| | |
|---|---|
| Nα-Boc-L-Lys(Cbz)-Nip-β-Ala-OBn | (CP #1); |
| Nα-Boc-L-Lys-Nip-β-Ala-OH | (CP #2); |

Nα-Boc-D-Lys-Nip-β-Ala-OH (CP #3);

Nα-Boc-L-Arg-Nip-β-Ala-OH (CP #8);

Nα(-Boc-L-Lys-Nip-γ-aminobutyric acid (CP #9);

Nα-Boc-D-Lys-Nip-γ-aminobutyric acid (CP #11);

Nα-Boc-D-Lys-Nip-Gly-OH (CP #12);

Nα-Boc-D-Lys-S-(+)-Nip-β-Ala-OH (CP #14);

Nα-Boc-L-Lys(i-Pr)-Nip-β-Ala-OH (CP #15);

Nα-Boc-D-Lys-R-(−)-Nip-β-Ala-OH (CP #16);

N-[3-(4-Piperidinepropionyl]-Nip- β-Ala-OH (CP #17);

Nα-Boc-D-Lys-Nip-L-Asp-OMe (CP #18);

or

N-(Nε-Aminocaproyl)-3-piperidinemethylaminopropronic acid (CP #19).

* * * * *